US007872105B2

(12) United States Patent
Mackenzie et al.

(10) Patent No.: US 7,872,105 B2
(45) Date of Patent: Jan. 18, 2011

(54) ANTICARCINOMA ANTIBODIES AND USES THEREOF

(75) Inventors: Colin Roger Mackenzie, Ottawa (CA); Jianbing Zhang, Ottawa (CA); Thanh-Dung Nguyen, Ottawa (CA); Qinggang Li, Ottawa (CA); Kien Trung Mai, Ottawa (CA)

(73) Assignees: National Research Council of Canada, Ottawa (CA); Ottawa Hospital Research Institute, Ottawa (CA)

( * ) Notice: Subject to any disclaimer, the term of this patent is extended or adjusted under 35 U.S.C. 154(b) by 50 days.

(21) Appl. No.: 11/440,137

(22) Filed: May 25, 2006

(65) Prior Publication Data

US 2006/0286113 A1 Dec. 21, 2006

Related U.S. Application Data

(63) Continuation-in-part of application No. PCT/CA2004/001488, filed on Aug. 17, 2004, and a continuation-in-part of application No. 10/547,528, filed as application No. PCT/CA2004/000309 on Mar. 2, 2004, now abandoned.

(51) Int. Cl.
*C07K 16/00* (2006.01)
(52) U.S. Cl. .................... 530/388.1; 530/388.8
(58) Field of Classification Search ........................ None
See application file for complete search history.

(56) References Cited

U.S. PATENT DOCUMENTS

| | | | |
|---|---|---|---|
| 5,593,847 A | 1/1997 | Barnett et al. | |
| 5,777,078 A | 7/1998 | Bayley et al. | |
| 5,798,218 A | 8/1998 | Buckley | |
| 5,817,771 A | 10/1998 | Bayley et al. | |
| 5,824,776 A | 10/1998 | Bayley et al. | |
| 5,874,298 A * | 2/1999 | Johnson et al. | 435/325 |
| 6,190,657 B1 | 2/2001 | Pawelek et al. | |
| 2002/0039581 A1 | 4/2002 | Carreno et al. | |
| 2002/0045736 A1 | 4/2002 | Yu et al. | |
| 2002/0077454 A1 | 6/2002 | Yu et al. | |

FOREIGN PATENT DOCUMENTS

| WO | WO 94/25616 A1 | 11/1994 |
|---|---|---|
| WO | WO 96/20688 A2 | 7/1996 |
| WO | WO 97/20932 A | 6/1997 |
| WO | WO 98/20135 A2 | 5/1998 |
| WO | WO 00/52054 A | 9/2000 |
| WO | WO 00/58335 | 10/2000 |
| WO | WO 01/85777 A2 | 11/2001 |
| WO | WO 03/018611 A1 | 3/2003 |
| WO | WO 03/046560 | 6/2003 |
| WO | WO 03/048304 | 6/2003 |
| WO | WO 03/055527 | 7/2003 |
| WO | WO 2004/078097 | 9/2004 |

OTHER PUBLICATIONS

Harmsen et al, Appl Microbiol Bioteclinol, 2007, 77:13-22.*
Rudikoff et al, Proc. Natl. Acad. Sci. USA, 79(6):1979-1983, Mar. 1982.*
MacCallum et al, J. Mol. Biol., 262, 732-745, 1996.*
Casset et al, Biochemical and Biophysical Research Communications, 307:198-205, 2003.*
Coleman P. M., Research in Immunology, 145:33-36, 1994.*
Definition of contiguous, Merriam Webster online dictionary, Jan. 31, 2009.*
Brichory, F., et al., "Proteomics-based Identification of Protein Gene Product 9.5 as a Tumor Antigen . . . " Cancer Research (2001) 61:7908-7912.
Casset, F., et al., "A peptide mimetic of an anti-CD4 monoclonal antibody by rational design" Biochemical and Biophysical Research Communication (2003) 307:198-205.
Colman, P.M., et al., Effects of amino acid sequence changes on antibody-antigen interactions Biomolecular Research Inst. (1994) 145:33-36.
Efimov, V.P., et al., "The thrombospondin-like chains of cartilage oligomeric matrix . . . " Biophysical Chemistry (1994) 341"54-58.
Els Conrath, K., et al., "Camel Single-domain Antibodies as Modular Building . . . " Biological Chemistry (2001) 276:7346-7350.
Frankel, A.E., et al., "Antibody-Toxin Hybrids: A Clinical Review of their use" Biological Response Modifiers (1985) 4:437-446.
Griffiths, A.D., et al., "Isolation of high affinity human antibodies directly . . . " EMBO Journal (1994) 13:3245-3260.
Hoogenboom, H.R., et al., "Natural and disgner binding sites made by phage display technology" Immunology (2000) 21:371-378.
Howard, S.P., et al., "Nucleotide Sequence of the Gene for the Hole-Forming . . . " Journal of Bacteriology (1987) 169:2869-2871.
Hudson, P.J., et al., "High avidity scFv multimers; diabodies and triabodies" Journal of Immunological Methods (1999) 231:177-189.
Kaminski, M.J., et al., "The Role of Homophilic Binding in Antitumor Antibody . . . " Biological Chemistry (1999) 274:5597-5604.
Kitov, P.I., et al., "Shiga-like toxins are neutralized by tailored multivalent carbohydrate ligands" Letters to Nature (2000) 403:669-672.
Ling, H., et al., "Structure of the Shiga-like toxin I B-Pentamer Complexed with an Analogue . . . " Biochemistry (1998) 37:1777-1788.
MacCallum, R.M., et al., "Antibody-antigen Interactions: Contact Analysis and Binding Site Topography" J.Mol. Biol. (1996) 262:732-745.
McCafferty, J., et al., "Phage antibodies: filamentous phage displaying antibody variable domains" Nature ( 1990) 348:552-554.

(Continued)

*Primary Examiner*—Misook Yu
*Assistant Examiner*—Mark Halvorson
(74) *Attorney, Agent, or Firm*—Sonia Patenaude; Christine Piché; Hans Koeing

(57) ABSTRACT

A novel single domain antibody AFAI and fragments thereof which has specific affinity for binding to carcinoma, and especially lung carcinoma. This antibody, and portions thereof, can be used, inter alia in the diagnosis and treatment of carcinoma.

16 Claims, 8 Drawing Sheets

OTHER PUBLICATIONS

Menon, L.G., et al., "Inhibition of lung metastasis in mice induced by B16F10 melanoma cells by polyphenolic compounds" Cancer Letters (1995) 95:221-225.

Ohlin, M., et al., "Light Chain Shuffling of a High Affinity Antibody Results in a Drift in Epitope Recognition" Molecular Immunology (1996) 33:47-56.

Pluckthun, A., et al., "New protein engineering approaches to multivalent and bispecific antibody fragments" Immunotechnology (1997) 3:83-105.

Rudikoff, S., et al., "Single amino acid substitution altering antigen-binding specificity" Proc. Natl. Acad. Sci (1982) 79:1979-1983.

Schier, R., et al., "Isolation of Picomolar Affinity Anti-c-erbB-2 Single-chain Fv by Molecular Evolution . . . " J. Mol. Biol. (1996) 263:551-567.

Skerra, A., et al., "The functional expression of antibody Fv Fragments in *Escherichia coli*: . . . " Nature Publishing Group (1991) 9:273-278.

Soltyk, A.M., et al., "A Mutational Analysis of the Globotriaosylceramide-binding Sites of Verotoxin VT1" Biological Chemistry (2002) 277:5351-5359.

Spyres, L.M., et al. "Cytosolic Delivery and Characterization of the TedB Glucosylating Domain by Using a Heterologous Protein Fusion" Infection and Immunity (2001) 69:599-601.

Tanha, J., et al., "Optimal Design Features of Camelized Human Single-domain Anitbody Libraries" Biological Chemistry (2001) 276:24772-24780.

Tanha, J., et al., "Selection by Phage display of llama conventional VH fragments with heavy . . . " Immunological Methods (2002) 263:97-109.

Tanha, J., et al., "Phage Display Technology for Identifying Specific Antigens on Brain Endothelial Cells" Methods in Molecular Medicine (2003) 89:435-449.

Terskikh, A.V., et al., "Peptabody: A New type of high avidity binding protein" Proc. Natil. Acad. Sci. (1997) 94:1663-1668.

Willuda, J., et al., "High Thermal Stability is Essential for Tumor Targeting of Antibody Fragments: . . . " Cancer Research (1999) 59:5758-5767.

Yang, W.P., et al., "CDR Walking Mutagenesis for the Affinity Maturation of a Potent Human Anti-HIV-1 Antibody into the Picomolar Range" Mol. Biol. (1995) 254:392-403.

Zhang, J., et al., "Pentamerization of Single-domain Antibodies from Phage Libraries: . . . " Mol. Biol. (2004) 335:49-56.

Zhang, J., et al., "A Pentavalent Single-domain Antibody Approach to Tumor Antigen Discovery and the . . . " J. Mol. Biol. (2004) 341:161-169.

Zimmermann, S., et al., "A novel immunotoxin recognising the epithellal glycoprotein-2 has potent antitumoural . . . " Cancer Immunol Immunother (1997) 44:1-9.

Jantscheff, P., "Expression of CEACAM6 in resectable colorectal cancer: a factor of independent prognostic significance" Nal. of Clinical Oncology (2003) 21:3638-3646.

Kuroki, M., et al., "Nonspecific cross-reacting antigen-50/90 (NCA-50/90) as a new tumor marker" Anticancer Research (1999) 19:5599-5606.

Pimenidou, A., et al., "Bacteriophage-derived antibodies in cancer research-diagnosis imaging and treatment" Disease Markers (2000) 16:41-51.

Schoelzel, S., et al., "Carcinoembryonic antigen family members CEACAM6 and CEACAM7 are differentially expressed . . . " American Journal of Pathology (2000) 156:595-605.

* cited by examiner

DVQLQASGGGVVQPGGSLRLSCAAHDPIFDKNLMGWGR
QAPGKQREYVATISGSGGTNYASSVEGRFTISRDNAKK
TVYLQMNDLKPEDTAVYYCNSAFAIWGQGTQVTVSS

B

AFAI    [ AFAI | T ]            50 AA

ES1     [ AFAI | L | VT1B | R | T ]

AFAI:   The sdAb AFAI
VT1B:   The D17E/W34A of verotoxin B subunit (VT1B),
        accession number of VT1B:p08027, AA21-89
T:      c-Myc and 5 X His tag, EQKLISEEDLNHHHHH
L:      Left linker, GPGGGSGGGGS
R:      Right linker, GGGGSGLAGS

C

DVQLQASGGGVVQPGGSLRLSCAAHDPIFDKNLM
GWGRQAPGKQREYVATISGSGGTNYASSVEGRFT
ISRDNAKKTVYLQMNDLKPEDTAVYYCNSAFAIW
GQGTQVTVSSGPGGGSGGGGSTPDCVTGKVEYTK
YNDEDTFTVKVGDKELFTNRANLQSLLLSAQITG
MTVTIKTNACHNGGGFSEVIFRGGGGSGLAGSEQ
KLISEEDLNHHHHH

D (kDa)        1    2
113 —
 92 —
 53 —
 35 —
 29 —
 22 —

SEQUENCE LISTING

<160> NUMBER OF SEQ ID NOS: 9

<210> SEQ ID NO 1
<211> LENGTH: 112
<212> TYPE: PRT
<213> ORGANISM: Artificial Sequence
<220> FEATURE:
<223> OTHER INFORMATION: Description of Artificial Sequence: AFAI amino
      acid sequence

<400> SEQUENCE: 1

Asp Val Gln Leu Gln Ala Ser Gly Gly Gly Val Val Gln Pro Gly Gly
 1               5                  10                  15

Ser Leu Arg Leu Ser Cys Ala Ala His Asp Pro Ile Phe Asp Lys Asn
            20                  25                  30

Leu Met Gly Trp Gly Arg Gln Ala Pro Gly Lys Gln Arg Glu Tyr Val
        35                  40                  45

Ala Thr Ile Ser Gly Ser Gly Gly Thr Asn Tyr Ala Ser Ser Val Glu
    50                  55                  60

Gly Arg Phe Thr Ile Ser Arg Asp Asn Ala Lys Lys Thr Val Tyr Leu
65                  70                  75                  80

Gln Met Asn Asp Leu Lys Pro Glu Asp Thr Ala Val Tyr Tyr Cys Asn
                85                  90                  95

Ser Ala Phe Ala Ile Trp Gly Gln Gly Thr Gln Val Thr Val Ser Ser
            100                 105                 110

<210> SEQ ID NO 2
<211> LENGTH: 218
<212> TYPE: PRT
<213> ORGANISM: Artificial Sequence
<220> FEATURE:
<223> OTHER INFORMATION: Description of Artificial Sequence: ES1 amino
      acid sequence

<400> SEQUENCE: 2

Asp Val Gln Leu Gln Ala Ser Gly Gly Gly Val Val Gln Pro Gly Gly
 1               5                  10                  15

Ser Leu Arg Leu Ser Cys Ala Ala His Asp Pro Ile Phe Asp Lys Asn
            20                  25                  30

Leu Met Gly Trp Gly Arg Gln Ala Pro Gly Lys Gln Arg Glu Tyr Val
        35                  40                  45

Ala Thr Ile Ser Gly Ser Gly Gly Thr Asn Tyr Ala Ser Ser Val Glu
    50                  55                  60

Gly Arg Phe Thr Ile Ser Arg Asp Asn Ala Lys Lys Thr Val Tyr Leu
65                  70                  75                  80

Gln Met Asn Asp Leu Lys Pro Glu Asp Thr Ala Val Tyr Tyr Cys Asn
                85                  90                  95

Ser Ala Phe Ala Ile Trp Gly Gln Gly Thr Gln Val Thr Val Ser Ser
            100                 105                 110

Gly Pro Gly Gly Gly Ser Gly Gly Gly Ser Thr Pro Asp Cys Val
            115                 120                 125

Thr Gly Lys Val Glu Tyr Thr Lys Tyr Asn Asp Glu Asp Thr Phe Thr
        130                 135                 140

Val Lys Val Gly Asp Lys Glu Leu Phe Thr Asn Arg Ala Asn Leu Gln
145                 150                 155                 160

Ser Leu Leu Leu Ser Ala Gln Ile Thr Gly Met Thr Val Thr Ile Lys
                165                 170                 175

Thr Asn Ala Cys His Asn Gly Gly Phe Ser Glu Val Ile Phe Arg
                180                 185                 190

Gly Gly Gly Gly Ser Gly Leu Ala Gly Ser Glu Gln Lys Leu Ile Ser
            195                 200                 205

Glu Glu Asp Leu Asn His His His His
    210                 215

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Phe Ala Ile
  1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Asn Leu Met Gly
  1               5

<210> SEQ ID NO 5
<211> LENGTH: 112
<212> TYPE: PRT
<213> ORGANISM: Artificial Sequence
<220> FEATURE:
<223> OTHER INFORMATION: Description of Artificial Sequence: Formula
      peptide sequence
<220> FEATURE:
<221> NAME/KEY: MOD_RES
<222> LOCATION: (11)
<223> OTHER INFORMATION: Val, Ser, Asp, Leu, Phe, Trp or Thr
<220> FEATURE:
<221> NAME/KEY: MOD_RES
<222> LOCATION: (37)
<223> OTHER INFORMATION: Gly, Phe, Tyr Val, Ile, His or Leu
<220> FEATURE:
<221> NAME/KEY: MOD_RES
<222> LOCATION: (44)
<223> OTHER INFORMATION: Gln, Gly, Glu, Asp, Leu, Arg or Lys
<220> FEATURE:
<221> NAME/KEY: MOD_RES
<222> LOCATION: (45)
<223> OTHER INFORMATION: Arg, Cys, Gln, Leu, Ile, Pro or Lys
<220> FEATURE:
<221> NAME/KEY: MOD_RES
<222> LOCATION: (47)
<223> OTHER INFORMATION: Tyr, Thr, Ala, Trp, Phe, Ser or Leu
<220> FEATURE:
<221> NAME/KEY: MOD_RES
<222> LOCATION: (102)
<223> OTHER INFORMATION: Trp, Arg, Glu, Ala, Gly, Val or Lys

<400> SEQUENCE: 5

Asp Val Gln Leu Gln Ala Ser Gly Gly Gly Xaa Val Gln Pro Gly Gly
  1               5                  10                  15

Ser Leu Arg Leu Ser Cys Ala Ala His Asp Pro Ile Phe Asp Lys Asn
             20                  25                  30

```
Leu Met Gly Trp Xaa Arg Gln Ala Pro Gly Lys Xaa Xaa Glu Xaa Val
         35                  40                  45

Ala Thr Ile Ser Gly Ser Gly Gly Thr Asn Tyr Ala Ser Ser Val Glu
     50                  55                  60

Gly Arg Phe Thr Ile Ser Arg Asp Asn Ala Lys Lys Thr Val Tyr Leu
 65                  70                  75                  80

Gln Met Asn Asp Leu Lys Pro Glu Asp Thr Ala Val Tyr Tyr Cys Asn
                 85                  90                  95

Ser Ala Phe Ala Ile Xaa Gly Gln Gly Thr Gln Val Thr Val Ser Ser
            100                 105                 110

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Ile Ser Gly Ser Gly Gly Thr Asn Tyr Ala Ser Ser Val Glu Gly
  1               5                  10                  15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Gln Lys Leu Ile Ser Glu Glu Asp Leu Asn His His His His His
  1               5                  10                  15

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Pro Gly Gly Gly Ser Gly Gly Gly Gly Ser
  1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Gly Gly Gly Ser Gly Leu Ala Gly Ser
  1               5                  10
```

ANTICARCINOMA ANTIBODIES AND USES THEREOF

CROSS REFERENCE TO RELATED APPLICATIONS

This application is a continuation-in-part of international application Number PCT/CA2004/001488 filed 17 Aug. 2004 and a continuation-in-part of U.S. application Ser. No. 10/547,528 filed 31 Aug. 2005 now abandoned which entered the national phase based upon PCT/CA2004/000309 filed Mar. 2, 2004.

BACKGROUND TO THE INVENTION

It is widely expected that proteomic research will greatly facilitate the discovery of novel tumor targets. Major advances have been made in the identification of targets for diagnostic purposes. However, limitations of the present technologies have hindered identification of new therapeutic targets. The techniques commonly employed in proteomics, such as two-dimensional gel electrophoresis, Liquid Chromatography Tandem Mass Spectrometry (LC/MS/MS), Matrix-Assisted Laser Desorption Ionization/Mass Spectrometry (MALDI-MS), and the yeast two-hybrid system have not met the demand for "drugable" targets, such as cell surface markers.

Tumor targeting antibodies and peptides can be isolated by library display approaches (e.g. Aina, 2002; Hoogenboom, 1998). This is usually accomplished by screening a phage display library, or libraries with other display formats, against purified tumor specific or tumor associated antigens. However, tumor targeting antibodies and peptides have also been isolated by panning libraries against tumor cells or tumor tissues without prior information on the molecular targets. Noteworthy advantages of the latter approach are: (i) the isolated antibodies/peptides bind to native forms of their antigens/ligands on the cell surface whereas purified tumor antigens are often recombinant in nature and lack post-translational modification, (ii) the antigens are accessible to the isolated antibodies/peptides whereas those isolated by panning against pure antigens may recognize epitopes which are naturally buried in the membrane or blocked by carbohydrate modification. However, antibodies/peptides isolated with this method usually have a low to moderate affinity to their antigens/ligands.

Since each M13 phage particle presents five copies of the minor coat protein pIII, a phage particle displaying an antibody fragment on all copies of pIII can be considered a pentavalent antibody. This multivalent display of antibody fragments on phage greatly increases the avidity of the antibody and facilitates both screening and evaluation of phage antibodies. Isolated antibody fragments (scFvs or sdAbs) or peptides bind antigen much less efficiently since they exist primarily in a monovalent form and lack avidity.

An antibody fragment oligomerization strategy that permits pentavalency as in pIII phage display is the subject of PCT/CA02/01829 (MacKenzie and Zhang). Fusion of a single domain antibody (sdAb) to the homo-pentamerization domain of the B subunit of verotoxin (VT1B) results in the simultaneous pentamerization of the sdAb. The pentavalent sdAbs, termed pentabodies, bind much more strongly to immobilized antigen than their monomeric counterparts. In the instance of peptide hormone-binding sdAb, pentamerization resulted in $10^3$ to $10^4$-fold improvement in binding to immobilized antigen.

It is an object of the invention to provide a single-domain antibody with affinity for lung carcinoma.

SUMMARY OF THE INVENTION

There is provided herein a novel single domain antibody AFAI and fragments thereof which has specific affinity for binding to carcinoma, and especially lung carcinoma. This antibody, and portions thereof, can be used, inter alia in the diagnosis and treatment of carcinoma.

BRIEF DESCRIPTION OF THE DRAWINGS

A better understanding of the invention will be obtained by considering the detailed description below, with reference to the following drawings in which:

FIG. 1 is a depiction of monomeric and pentameric AFAI. (a) Sequence of AFAI (SEQ ID NO:1) with CDR1, CDR2 and CDR3 underlined; (b) Schematic of the primary structures of the monomeric (AFAI) and pentameric (ES1) proteins. The sequences of the left (SEQ ID NO:8) and right (SEQ ID NO:9) linkers, as well as the c-Myc and 5×His tag (SEQ ID NO:7), are shown; (c) sequence of ES1 (SEQ ID NO:2) with AFAI underlined; (d) SDS-PAGE of purified ES1 (lane 1) and AFAI (lane 2).

DETAILED DESCRIPTION

Figure 2:
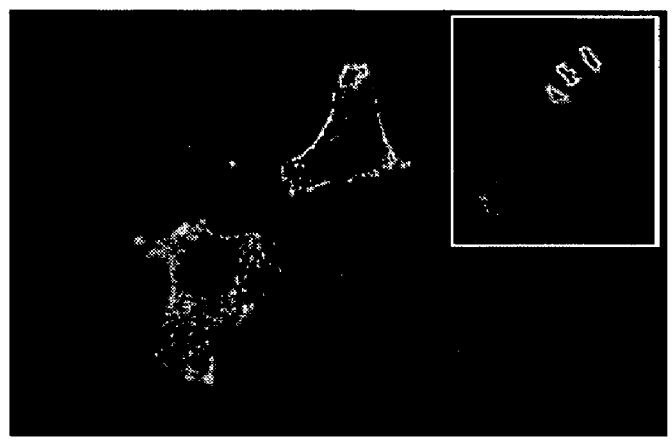
FIG. 2 is a pictorial depiction of immunocytochemical staining of A549 cells with the AFAI phage antibody. Cells were exposed to the AFAI phage as the first antibody, mouse anti-M13 IgG as the second antibody and Alexa Fluor 546 labeled goat anti-mouse IgG as the third antibody. DAPI and $DiOC_5(3)$ were used to stain cell nuclei and endoplasmic reticulum, respectively.

Proteomics research has delivered many novel tumor targets. However, due to some limitations, it has been difficult to identify targets that are most accessible for drug application. A novel tumor antigen discovery platform based on screening a single domain antibody (sdAb) library against tumor cells and subsequently identifying the corresponding antigens of the isolated antibodies is described herein. A specific sdAb, AFAI, specific for non-small cell lung carcinoma (A549 cell line) was isolated from a phage library derived from the heavy chain antibody repertoire of a llama as described in Example 1. The homopentamerization property of a non-toxic verotoxin B-subunit was exploited to make the ES1 pentabody, the pentameric forms of AFAI. Pentamerization dramatically improved the binding of the AFAI to A549 cells. Immunohistostaining showed that ES1 is highly specific for lung carcinoma.

It is possible in light of the disclosure herein to chemically syntesize the whole gene for ES1 and express it in *E. coli* or another suitable organism according to standard techniques. The gene of AFAI SEQ ID NO.2 can be synthesized from ES1, which is the binding entity to its antigen. It is possible, in light of the disclosure herein, to make dimeric, trimeric, tetrameric, other pentameric and other multivalent forms of AFAI SEQ ID NO.3. Such products can be useful in methods and compositions relating to the present invention, as can DNA and clone material providing variants of such products which provide specific binding to a malignant tissue or cells of interest, as described herein.

ES1, AFAI and/or variants thereof showing similar binding specificity ("suitable variants") are useful in the diagnosis and treatment of lung carcinoma. Diagnostic methods with which ES1, AFAI and/or suitable variants thereof can be used include: immunohistochemical methods; labeling the molecule(s) (ES1, AFAI, variants) with radio isotopes and detecting with tumor imaging tools such as positron emission tomography and MRI; analysis of blood samples (and detecting binding using standard techniques).

Diagnostic kits comprising ES1, AFAI and/or a suitable variant thereof and instructions for their use are specifically contemplated.

Therapeutic methods and compositions relating to ES1 and AFAI include employing AFAI, ES1, or a suitable variant thereof and, for example: labeling them with radio isotope and applying the molecules to a patient; conjugating them to one or more conventional therapeutics and applying the conjugate to a patient; conjugating them to one or more toxins and applying the conjugates to patients; expressing nucleic acid molecules encoding ES1, AFAI and/or a suitable variant thereof in a gene therapy vector and applying the vectors to patients.

Results

EXAMPLE 1

Cell Culture

The non-small cell lung carcinoma cell line A549 was purchased from ATCC (Manassas, Va.) and maintained in DMEM (Gibco, Rockville, Mass.) supplemented with 5% FBS (Gibco) and 1% Antibiotic-Antimycotic (Gibco). Primary human dermal fibroblast cells were kindly provided by Dr. J. Xu (Apotex Research Inc. Ottawa, ON). Polyclonal rabbit anti-verotoxin antiserum was kindly provided by Dr. Clifford Lingwood (Univ. of Toronto).

Isolation of sdAb AFAI which Binds to Non-Small Cell Lung Carcinoma Cell Line A549

A naïve llama single domain antibody library (Tanha et al, 2002) served as the source of an antibody fragment specific for tumor cells, in this instance the non-small cell lung carcinoma cell line A549. The isolation of phage antibodies that bind to A549 cells, termed cell panning, was performed with A549 cells with pre-adsorption of the library on human fibroblasts at each round of panning.

An sdAb phage display library (Tanha et al, 2002) was panned with A549 as the target cells and human dermal fibroblasts as subtracting cells. The panning was performed as described in Becerril et. al. (1999) with slight modifications. For the first round of panning, $10^{13}$ pfu were incubated with the subtracting fibroblast cells to remove fibroblast-binding phage. Phage particles remaining in the supernatant were incubated with A549 cells cultured in a 5 cm petri dish at room temperature for 1 hr. The A549 cells were washed 5 times, 1 minute each, with PBS and 5 times, 10 minutes each, with stripping buffer (50 mM glycine, pH 2.8, 0.5 M NaCl, 2 M urea, 2% polyvinylpyrolidone) and then lysed with 100 mM triethylamine. The cell lysate was neutralized by the addition of 100 µl of 1 M Tris (pH 7.0). Phage in the neutralized cell lysate were amplified in *E. coli* TG1 cells. The amplified sub-library was subjected to the next round of panning employing the same method. Individual phage clones were selected after four rounds of panning and the DNA sequences encoding the displayed antibodies were determined.

Individual phage clones were isolated after four rounds of panning and the cell binding activities of the phage clones were examined by ELISA. Of 94 clones, 25 clones tested positive. Sequence analysis of the ELISA-positive phage clones showed that all 25 positive phage clones displayed the same sdAb. This antibody was designated AFAI because the CDR3 region of the antibody is the tetrapeptide Ala-Phe-Ala-Ile (SEQ ID NO:3; FIG. 1).

EXAMPLE 2

Cell Staining Part A: Cell Staining with Phage Displayed AFAI

When A549 cells were immunostained with AFAI phage as the first antibody followed by an anti-M13 monoclonal antibody and Fluor 546 labeled goat anti-mouse IgG it was observed that very intense fluorescent signals were associated with a cell sub-population (FIG. 2). The staining pattern of the positive A549 cells suggested that AFAI binds to an abundant membrane antigen.

To investigate whether the binding of AFAI phage to A549 cells is cell type specific, a human bronchial epithelial cell line, HBE4, a human prostate cell line, PREP and a primary human fibroblast cell line were chosen as controls for immunocytochemical staining. Under the same conditions employed for A549 immunocytochemistry, no staining was observed with human fibroblasts and only very weak staining was observed with HBE4 and PREP.

EXAMPLE 3

Cell Staining Part B: Production of Monomeric and Pentameric AFAI sdAbs and Cell Staining with the sdAbs For further evaluation and characterization of AFAI, monomeric and pentameric AFAI were expressed and purified. The gene encoding AFAI was amplified by PCR and inserted into an *E. coli* expression vector, generating clone pAFAI (FIG. 1B). To exploit the high avidity effect of pentabodies, a pentameric form of AFAI, designated ES1, was constructed (FIG. 1B and FIG. 1C). The yields of purified AFAI and ES1 (FIG. 1D) from 1 liter flask cultures of *E. coli* TG1, without fermentation optimization, were 6 mg and 20 mg, respectively.

Briefly, DNA encoding sdAb AFAI was cloned into the BbsI/BamHI sites of plasmid pSJF2 (Tanha, 2003) and BbsI/ApaI sites of plasmid pVT2 to generate expression vectors for monomeric and pentavalent AFAI, respectively. The obtained *E. coli* clones were designated pAFAI (monomer) and pES1 (pentamer). Proteins AFAI and ES1 were produced as described in Tanha et. al. (2003) with the modification of protein extraction from *E. coli* cells by cell lysis instead of osmotic shock. Briefly, the pAFAI and pES1 clones were inoculated into 100 ml M9 medium (0.2% glucose, 0.6% $Na_2HPO_4$, 0.3% $KH_2PO_4$, 0.1% $NH_4Cl$, 0.05% NaCl, 1 mM $MgCl_2$, 0.1 mM $CaCl_2$) supplemented with 0.4% casamino acids, 5 mg/l vitamin B1 and 200 µg/ml ampicillin and shaken overnight at 37° C. Thirty ml of the overnight M9 culture were transferred into 1 liter of M9 medium with the same supplements and shaken at 37° C. for 24 hours. Induction of gene expression was initiated by the addition of 100 ml 10× TB nutrients (12% Tryptone, 24% yeast extract, 4% glycerol), 2 ml of 100 mg/ml ampicillin and 1 ml of 1 M IPTG and the cultures were shaken at room temperature for 48 to 72 hours. *E. coli* cells were harvested by centrifugation and lysed with an Emulsiflex™ Cell Disruptor (Avestin Inc. Ottawa, ON). The cell lysate was centrifuged, the obtained clear supernatant was loaded onto a Hi-Trap™ Chelating Affinity Column (Amersham Biosciences, Piscataway, N.J.) and proteins containing $His_5$ tag were purified following the manufacturer's instructions.

Immunochemical staining of A549 cells was performed with both monomeric (AFAI) and pentameric (ES1) antibodies.

Standard immunochemical methods, with slight modifications, were employed in cell staining with AFAI phage and with monomeric and pentameric AFAI. Cells were grown on slide cover slips to approximately 70% confluence and fixed for 10 minutes with 4% formaldehyde in PBS. Permeabilization was carried out for 30 minutes at room temperature in 0.05% NP-40 (Bio-Rad, Hercules, Calif.) followed by three washes with PBS containing 0.05% Tween-20 (PBST). For cell staining with AFAI phage, $2\times10^{11}$ pfu of AFAI phage (in A549 medium) were incubated with fixed cells for 18 hours at 4° C. and washed three times, 5 minutes each, with PBST. For cell staining with monomeric or pentameric AFAI, 100 µg/ml of AFAI and ES1 (in A549 medium) were incubated with the cells for 2 hours at room temperature and washed three times with PBST. Secondary antibodies, monoclonal anti-M13 IgG (Amersham Biosciences) for M13 phage or the 9E10 anti c-myc IgG (ATCC) for the ES1 pentabody were applied at a 1:100 dilution for 30 minutes at room temperature followed by three washes with PBST. The third antibody, Alexa Fluor 546-labeled goat anti-mouse IgG™ (Molecular Probes, Inc. Eugene, Oreg.), was diluted 1:100 and applied in the same way as the secondary antibodies. Contrast staining was performed with DAPI and $(DiOC_5)_3$ (Molecular Probes). Following immunochemical staining cover slips were mounted using an Prolong Antifade Kit (Molecular Probes) and observed under an Olympus BX51™ fluorescent microscope and images were recorded.

Figure 3:
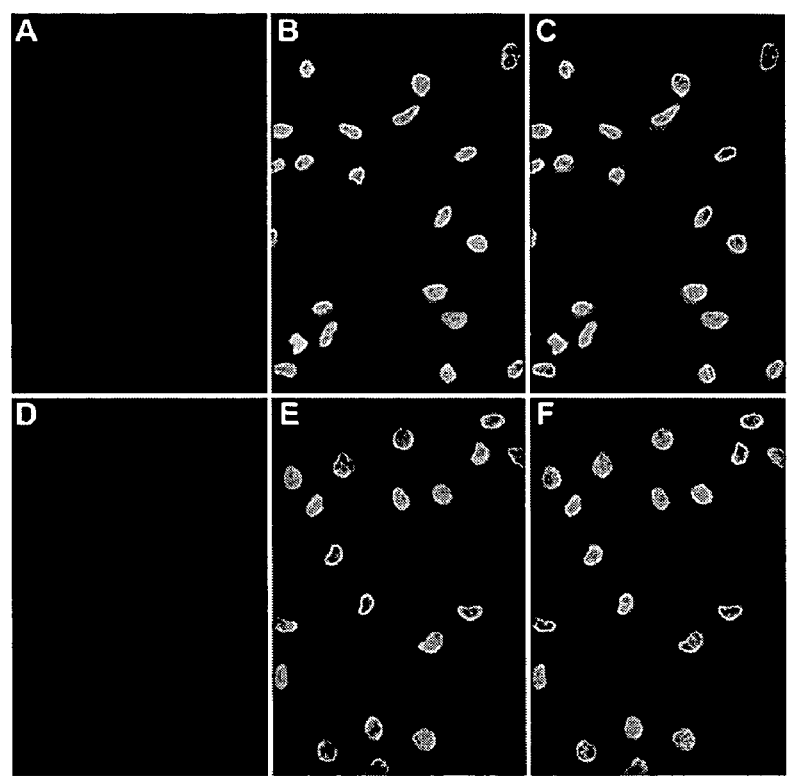
FIG. 3 is a pictorial depiction of immunocytochemical staining of A549 with AFAI and ES1. A549 cells were exposed to either ES1 (A) or AFAI (D) as the first antibody, monoclonal anti-c-myc IgG as the second antibody, Alexa Fluor 546 (red) labeled anti-mouse IgG as the third antibody. DAPI staining of (A) and (D) are shown in (B) and (E), respectively. Superimpositions of A, B and D, E are shown in C and F, respectively.

No obvious staining was observed when AFAI was employed (FIG. 3), probably because of the low binding affinity of monomeric AFAI. The ability of AFAI antibody to stain A549 cells was, however, observed when the pentameric form, ES1, was employed (FIG. 3). As observed with AFAI phage, ES1 stains only a sub-population of A549 cells.

EXAMPLE 4

Determination of Specificity of ES1 to Tumor Tissues

Figure 4:
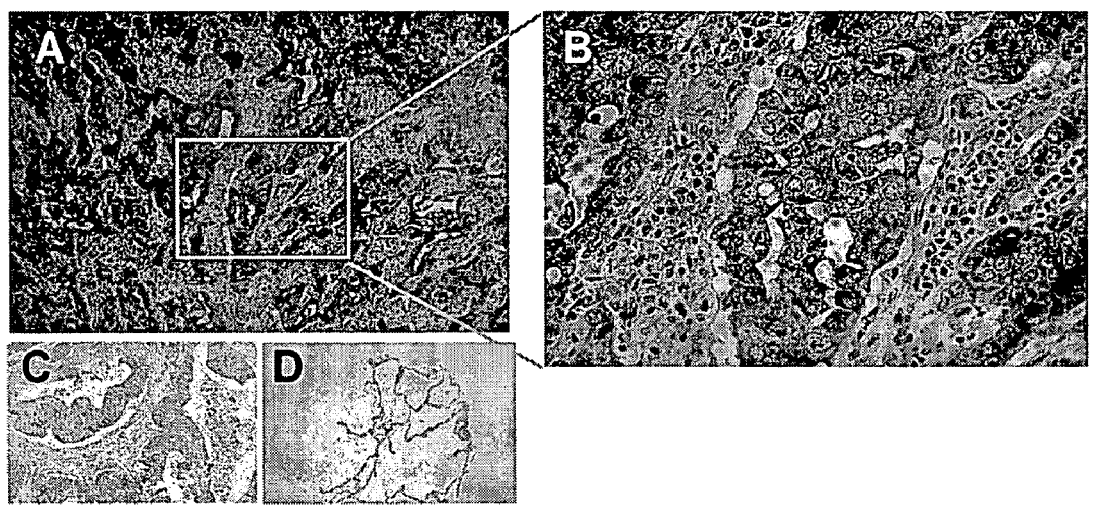
FIG. 4 is a pictorial depiction of immunohistochemical staining showing that ES1 binds strongly to differentiated lung adenocarcinoma and does not bind to most colon adenocarcinomas or to normal lung tissue. (A) Strong positive staining of a lung adenocarcinoma, (B) enlarged view of the boxed area in (A), (C) negative staining of a colon adenocarcinoma and (D) negative staining of normal lung tissue.

To determine the tissue specificity of ES1, immunohistochemical staining of a broad range of tissues on a tissue microarray using ES1 as primary antibody was performed. The results showed that ES1 recognized most lung adenocarcinomas by displaying a moderate to strong immunoreactivity. None of colon adenocarcinoma displayed strong immunoreactivity for ES1 however a focal weak to moderate immunoreactivity was observed in a few cases. Non cancerous lung and colon tissues were not immunoreactive (FIG. 4, Table 1).

Immunohistochemical Stains

To determine the tissue specificity of ES1, immunohistochemical staining of a broad range of tissues was performed using ES1 as primary antibody.

Immunostaining of human tissues using ES1 as the primary antibody was performed using the avidin-biotin peroxidase complex (ABC) method with an ABC kit (Vector Laboratories, Burlingame, Calif., USA) on four micron-thick sections cut from the paraffin blocks.

Immunostaining of human tissues using MIB1 (Dako, dilution 1:100) and TTF1 (Dako, dilution 1:50), two broadly used antibodies in lung carcinoma detection was performed using peroxidase-antiperoxidase technique.

Morphologic Evaluation

The immunoreactivity for ES1 was assessed by two pathologists and was scored as moderately or strongly positive staining when there was a continuous membranous and/or cytoplasmic staining pattern and as weakly positive when there was discontinuous membrane or weak cytoplasmic staining. The moderate or strong staining pattern was further scored as 3 in cases showing staining in more than 50%, 2 in more than 10% and 1 in up to 10% of cells. Cases with a discrepant score were reviewed.

One hundred-forty three resection or biopsy specimens containing tumors of lung, colon, breast stomach, pancreas, prostate, endometrium, ovary, thyroid and mesothelium were obtained (Table 1). For each case, one sample of representative tumor tissue, 2 mm in diameter, was removed from the paraffin block and re-embedded with other tumor samples to produce a tissue microarray paraffin block that contained at least 15 different tissues. Normal tissue was also sampled from non tumoral tissue distant from the tumor and from the normal autopsy lung tissue. Cases of lung, colon, breast stomach pancreas urinary bladder, gall bladder, esophagus and ovary with microarray tissue displaying negative, weak or focal immunoreactivity were re-submitted for immunostaining for ES1 using large tissue sections.

Table 2 compares the immunostaining results of the group of non-squamous large cell lung carcinomas with the combined group of colonic, mammary, urothelial carcinomas and other mucus-secreting adenocarcinomas. Excluding other types of carcinomas which showed weak or negative ES1 immunoreactivity, the sensitivity and the specificity of ES1 immunoreactivity for lung non-squamous large cell carcinomas were 97 and 45% respectively. The positive predictive value was 54%.

The results showed that ES1 displayed moderate to strong immunoreactivity with most lung adenocarcinomas. None of the colon adenocarcinomas displayed strong immunoreactivity with ES1; however, weak to moderate focal immunoreactivity was observed in a few cases. Non cancerous lung and colon tissues were not immunoreactive.

Figure 5:
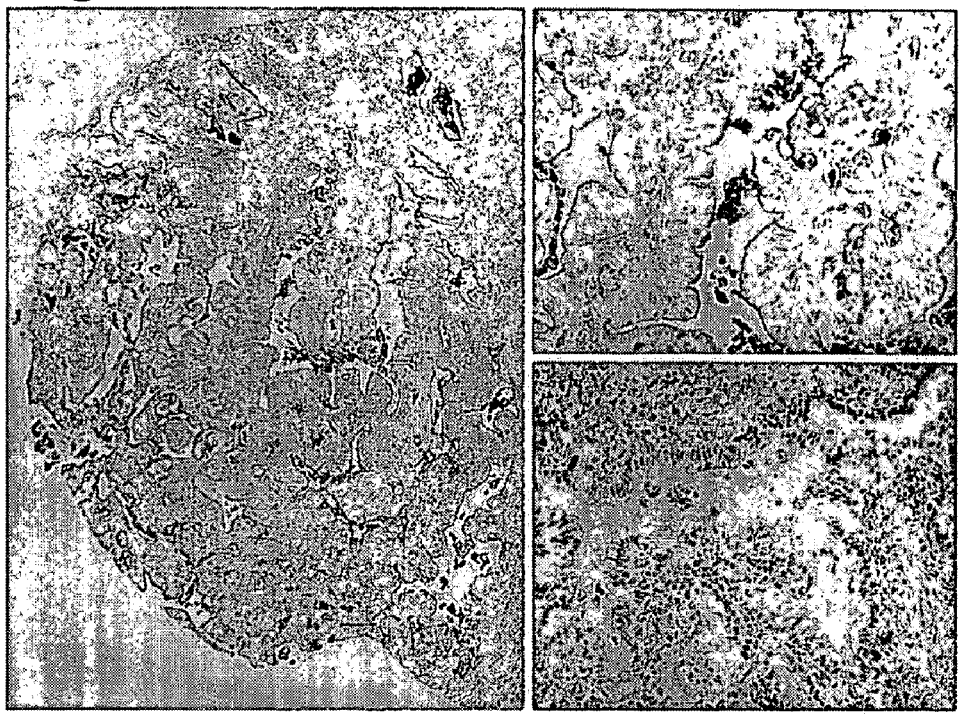
FIG. 5 is a depiction of bronchiolo-alveolar carcinoma of mucinous type: (A) Immunostaining for ES1 showing diffuse moderate immunoreactivity, mainly along luminal borders; (B) A high magnification of an area in A; (C) Immunostaining for TTF1 (DAKO) showing negative immunoreactivity.
Figure 6:
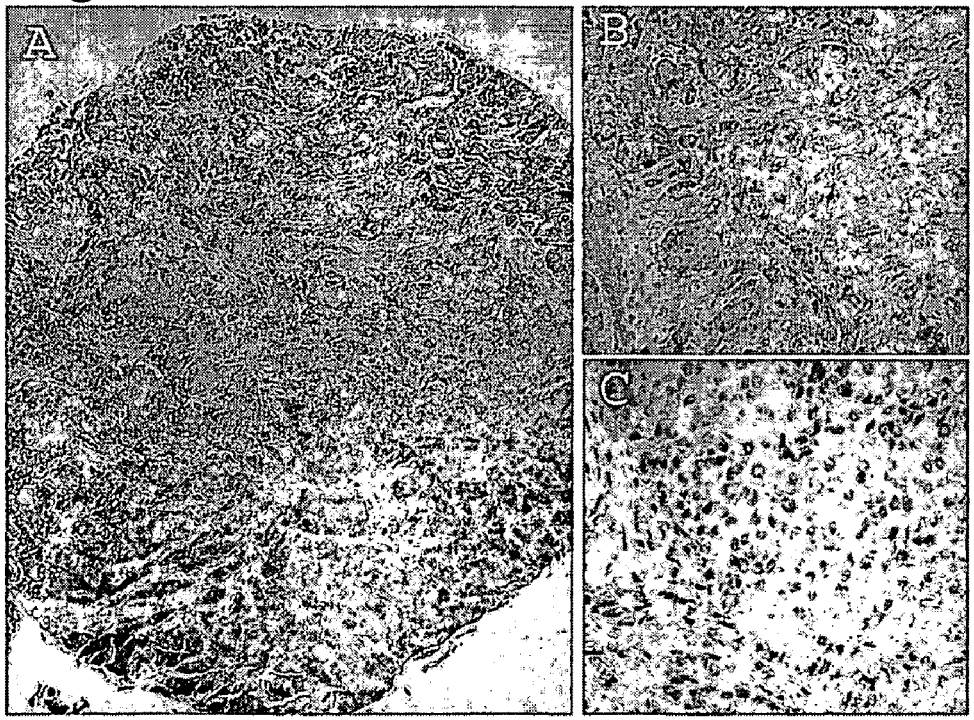
FIG. 6 is a depiction of metastatic poorly differentiated lung adenocarcinoma: (A) Immunostaining for ES1 showing diffuse strong immunoreactivity; (B) A high magnification of an area in A; (C) Immunostaining for TTF1 showing negative immunoreactivity.
Figure 7:
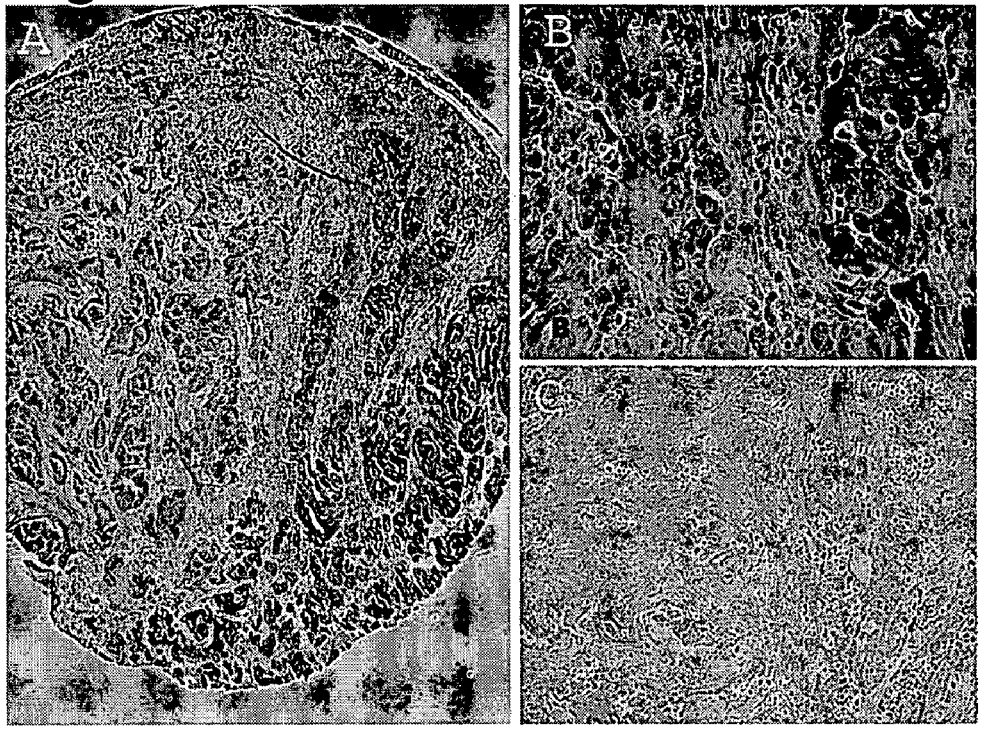
FIG. 7 is a depiction of Lung moderately differentiated adenocarcinoma: (A) Immunostaining for ES1 showing strong immunoreactivity in a focal area adjacent to an area displaying focal weak staining; (B) A high magnification of an area in A. (C) Immunostaining for MIB1 (DAKO) showing remarkable increase in immunoreactivity in an area with strong ES1 immunoreactivity.
Figure 8:
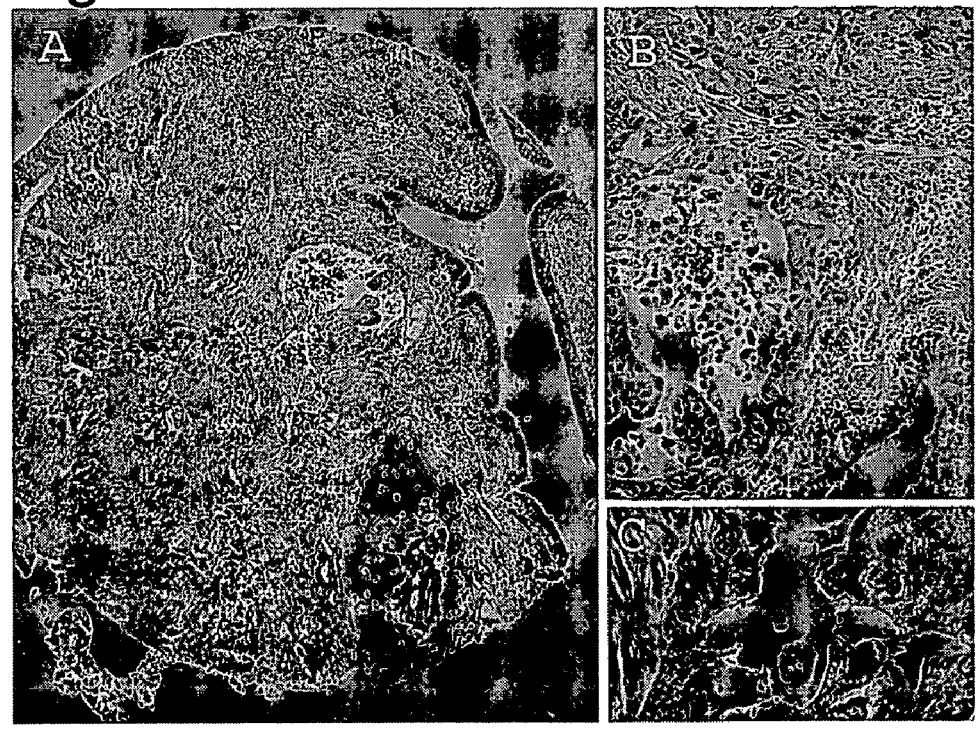
FIG. 8 is a depiction of lung poorly differentiated adenocarcinoma: (A) Immunostaining for ES1 showing moderate and extensive immunoreactivity; (B, C) High magnification of area in A. Note the negative immunostaining in the normal bronchial epithelium.

The reactivity was often stronger on the membrane (FIGS. 5,6,7) than in the cytoplasm (FIG. 8). The pattern of positive immunostaining varied from diffuse (FIGS. 5,6) to focal staining in portions of tumor or individual cells (FIGS. 7,8). Of 93 cases with negative, weak or focal immunoreactivity in microarray sections, there were eleven large sections showing a score of 1 or 2 immunoreactivity. Table 1 summarizes the final findings on immunostaining of all specimens.

Figure 9:
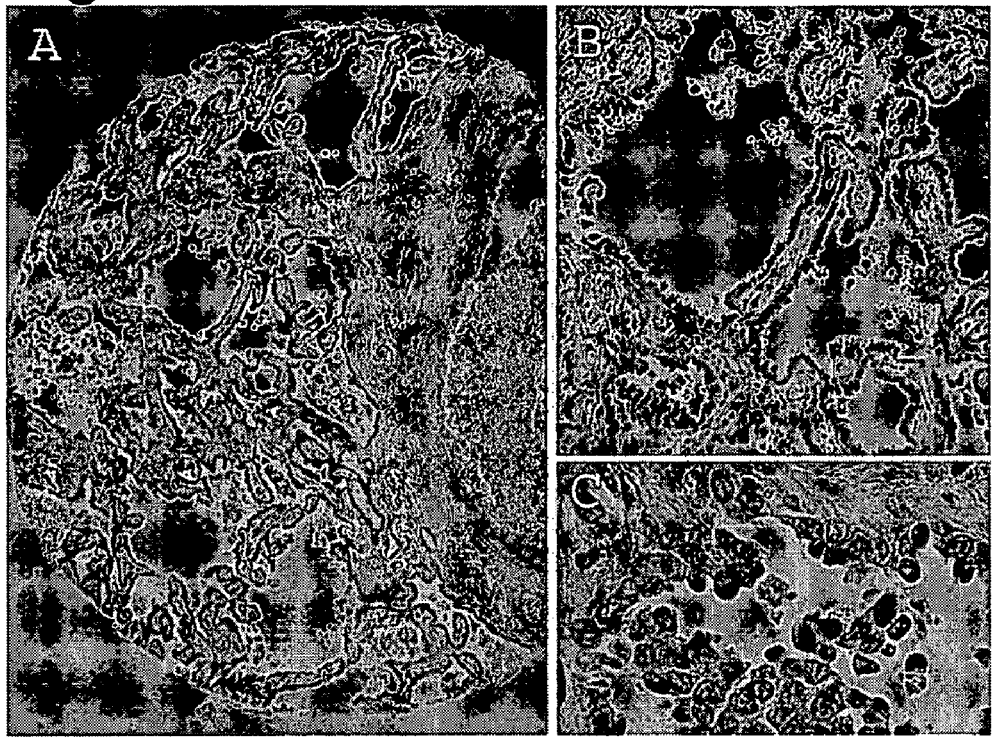
FIG. 9 is a depiction of lung Adeno-squamous carcinoma: (A) Immunostaining for ES1 showing focal immunoreactivity; (B, C) High magnifications of an area in A showing focal immunoreactivity.
Figure 10:
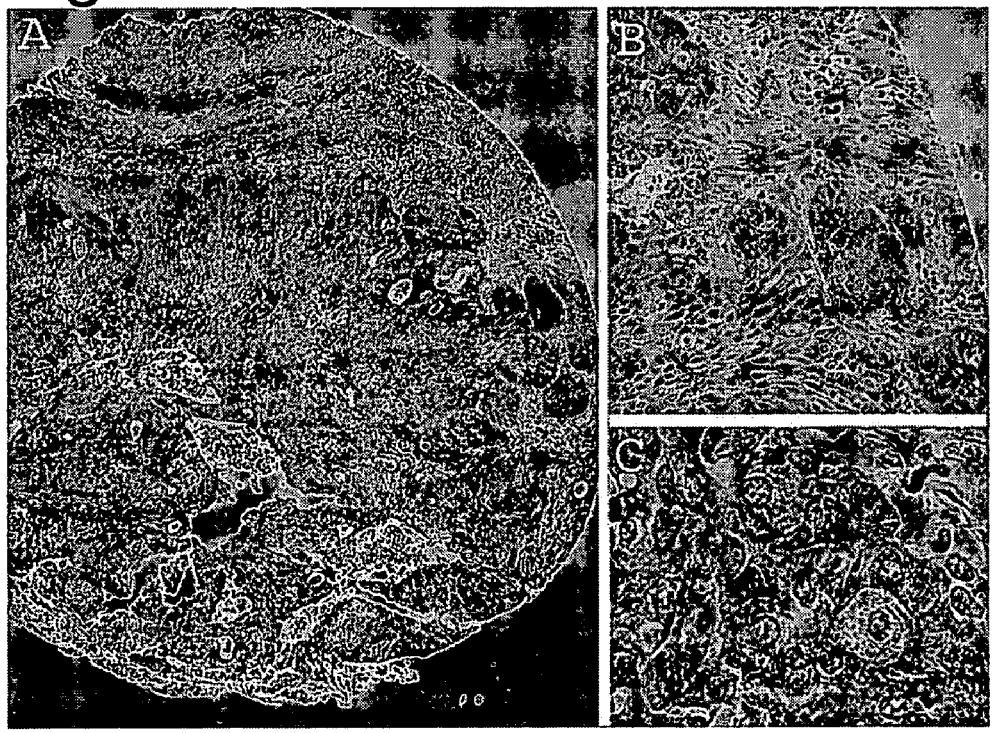
FIG. 10 is a depiction of a typical adenomatous hyperplasia of the lung: (A) Immunostaining for ES1 showing focal weak immunoreactivity, (B, C) High magnifications of an area in A showing weak immunoreactivity.

Thirty-five non-squamous large cell carcinomas of the lung including seven bronchiolo-alveolar carcinomas and 22 well to poorly-differentiated adenocarcinomas, six large cell undifferentiated carcinomas showed scores of 1, 2 and 3 immunoreactivity in 7, 17 and 10 tumors respectively (FIGS. 5 to 8). The remaining carcinoma was an undifferentiated large cell carcinoma with some features of squamous differentiation showing negative immunoreactivity. The tumors with focal moderate to strong immunoreactivity (less than 10% immunoreactive cells) were well-differentiated non-mucinous tumors. Two adeno-squamous carcinomas also displayed scores of 1 and 2 immunoreactivity in the adenocarcinoma component (FIG. 9). Four of five atypical adenomatous hyperplasias of the lung showed focal or weak immunoreactivity (FIG. 10). All pure squamous carcinomas, carcinoid tumors, normal and reactive lung parenchyma with or without accompanying carcinomas were not reactive for the antibody.

Figure 11:
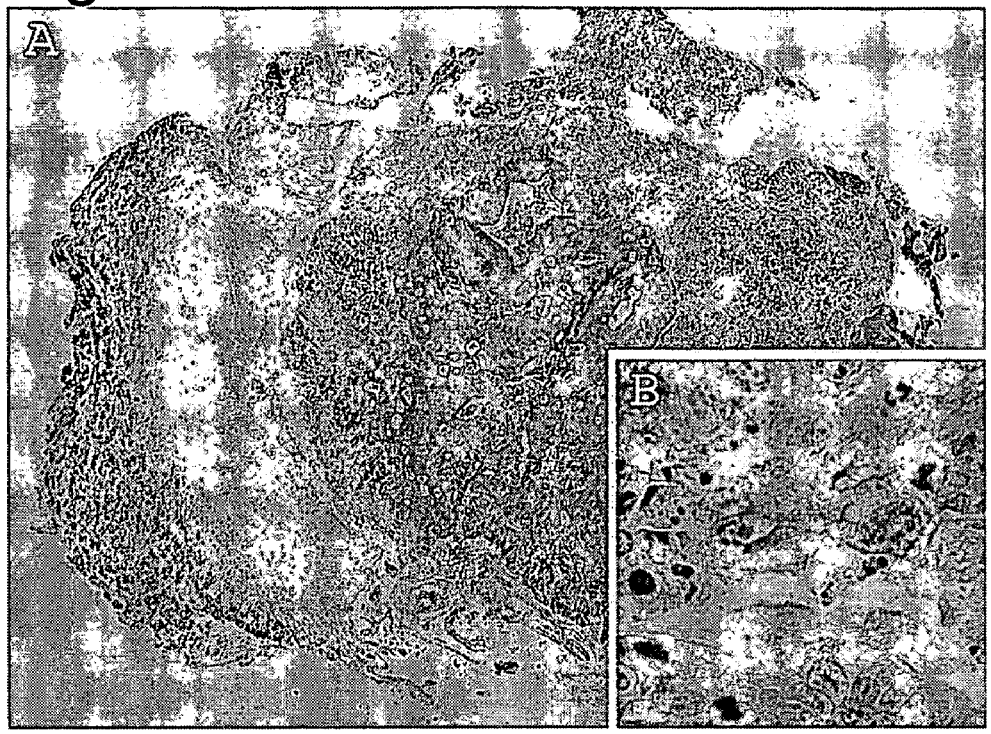
FIG. 11 is a depiction of metastatic moderately differentiated colonic adenocarcinoma in the brain: (A)Immunostaining for ES1 showing focal immunoreactivity in a few single cells; (B) A high magnification of an area in A.
Figure 12:
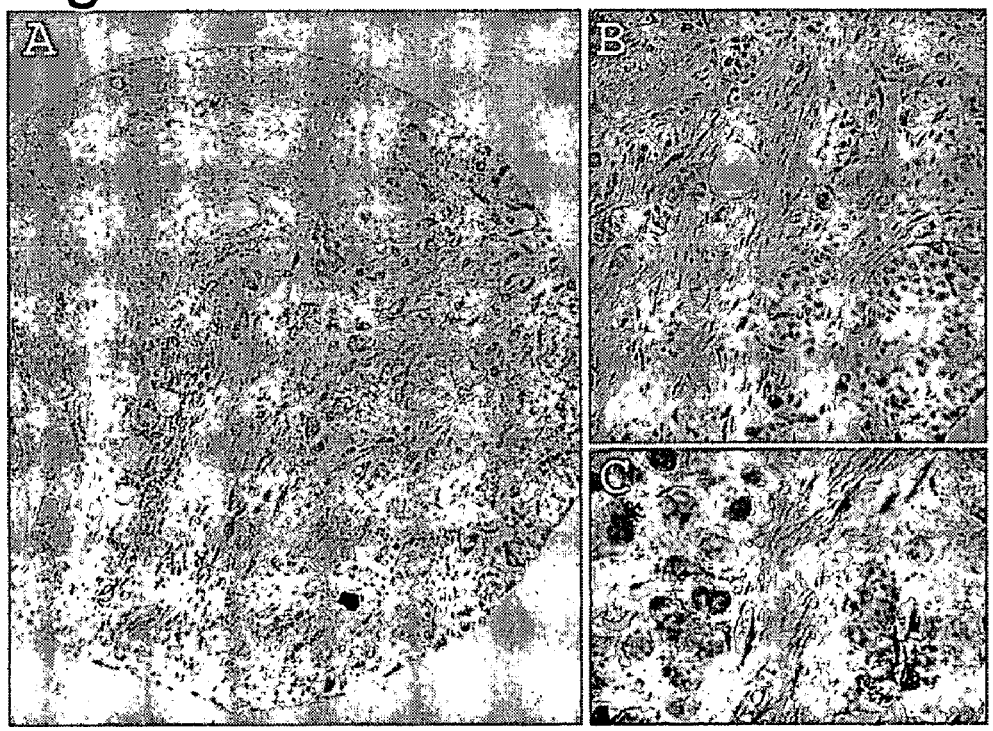
FIG. 12 is a depiction of infiltrating duct carcinoma of the breast: (A) Immunostaining for ES1 showing focal moderate immunoreactivity; (B) A high magnification of an area in A; (C) Focal strong immunoreactivity in a few acini in normal breast tissue.

For 53 non-lung and mucus-secreting tumor including 15 adenocarcinoma colonic adenocarcinomas, 8 breast carcinomas, 4 urothelial carcinomas and adenocarcinomas of the pancreas (six), stomach (six) and gallbladder (one), esophagus (three), urinary bladder (two), ovary (three) and trachea (one), the immunoreactivity was scored as 1, 2 , 3, weak and negative in 15, 11, 3, 12 and 12, respectively (FIGS. 11,12). Colonic adenocarcinomas formed the subgroup of tumor with more diffuse and strong immunoreactivity. Colonic adenomas only displayed focal or weak immunoreactivity.

For 32 non lung and non-mucinous tumors, the immunoreactivity was negative or weak. Normal tissues from lung, liver, pancreas, kidney, urinary bladder, endometrium, thyroid, esophagus and ovary from areas surrounding cancer or from organs not harboring cancer were not reactive for cancer with exception of one case of breast tissue (surrounding duct carcinoma) showing moderate positivity in occasional acini.

Immunostaining for MIB1 performed on 24 large sections of 24 non-squamous large cell lung carcinomas with score 1 or 2 immunoreactivity showed a remarkable increase in proliferativity of tumor cells in areas of large numbers of ES1-immunoreactive cells as compared to areas with negative, weak or focal ES1-immunoreactive cells. The immunostaining for TTF1 was performed on microarray tissue. All non-lung and non-thyroid tissue showed negative nuclear immunoreactivity. For 35 lung non-squamous large cell carcinomas, TTF1 immunoreactivity was negative in 8 cases including 5 undifferentiated large cell carcinomas, two poorly-differentiated adenocarcinomas and one mucinous bronchiolo-alveolar carcinoma. The other types of microarray tissue were not immunoreactive.

In this study, ES1 immunoreactivity was almost completely limited to malignant tumors, particularly lung adenocarcinomas. There was a tendency for the immunoreactivity to be stronger in lung tumors with a mucinous component as non-mucinous bronchiolo-alveolar carcinomas showed only focal immunoreactivity. ES1 immunoreactivity was positive in a number of colonic adenocarcinomas with weaker and more focal staining than in lung adenocarcinomas. Of interest, ES1 immunostaining remained scoring 2 or 3 for undifferentiated large cell lung carcinoma in the primary as well as in the metastatic sites as compared to low sensitivity of TTF1 in the immunostaining of the undifferentiated large cell lung carcinoma (*). Furthermore colonic adenomas showed only focal weak or negative immunoreactivity. Mucinous adenocarcinoma from other organs displayed score 2, focal or weak immunoreactivity in a small number of cases. The immunoreactive changes identified in the lung adenocarcinomas in this study likely correspond to an up-regulation of the AFAI antigen. This impression is supported by the finding of positive ES1 immunoreactivity in areas of carcinoma of the lung with increased proliferativity as demonstrated by the immunoreactivity for MIB1.

Non-Limiting Discussion of Variations and Uses of AFAI

The AFAI antigen, appears to be up-regulated in lung adenocarcinoma, even in less differentiated tumors. ES1 is likely a more sensitive marker for lung poorly differentiated lung adenocarcinoma than TTF1. Since most normal tissue tested were not ES1-immunoreactive, ES1 is suitable for use in the development of a screening test for lung adenocarcinomas and a number of colon and breast carcinomas.

In an embodiment of the invention there is provided an amino acid sequence of AFAI as shown in FIG. 1 or an amino acid sequence at least 90%, 95% or 98% identical to it. Examples of variant amino acid sequences of interest are shown in Table III in which unchanged residues are indicated by a hyphen. It will be appreciated that AFAI may be mutated at any position which does not interfere with antigen binding or specificity. Sites of particular interest include those for which some possible mutations are shown in Table III. While only some possible variants are shown, it will be appreciated that all functional variants, including all variants of AFAI differing from SEQ. ID. No. 1 by one or more of the amino acid changes depicted in Table III are specifically contemplated and fall within the scope of the invention.

In an embodiment of the invention there is provided an amino acid sequence having complete sequence identity to the underlined (CDR) regions of AFAI as shown in FIG. 1 and having at least 40%, 60%, 80%, or 90% sequence identity to the remaining portions of that sequence. Also provided are nucleic acid sequences encoding such amino acid sequences.

In an embodiment of the invention there is provided nucleic acid sequences encoding AFAI as disclosed in FIG. 1, or an amino acid sequence at least 90% or 95% identical to it. In an embodiment of the invention there is provided a nucleic acid sequence encoding a protein which has at least 70%, 80%, 90% 95%, or 98% sequence identity to the sequence of AFAI or ES1 as depicted in Table 2, or to a continuous 250 nucleic acid region thereof, or being complementary to any such nucleic acid sequence. In an embodiment of the invention there are provided PCR primers suitable for the amplification of a nucleic acid encoding AFAI or a portion thereof. In some instances the portion will include at least one CDR region.

In an embodiment of the invention there is provided a polypeptide sequence comprising at least 90 amino acids including at least one of the following three contiguous amino acid sequence: KNLMG SEQ ID No.4 TISGSGGTNYASS-VEG SEQ ID NO.6, and AFAI SEQ ID NO.3.

In an embodiment of the invention there is provided the use of an AFAI-derived polypeptide and/or a polypeptide having at least 90% identity to SEQ ID NO. 1 and/or a portion thereof in forming a conjugate by grafting the polypeptide to an antigen binding fragment. In some instances one or more of the AFAI CDR's is grafted onto an antigen binding fragment including, for example, a VHH, VH or VL framework (scaffold) or an immunoglobin and/or fragment thereof (e.g. Fab, scFv). One or more AFAI CDR's may also be used to produce a fusion protein wherein the second polypeptide sequence provides a useful functionality or property. In some instances it may be desired to produce humanized variants of the AFAI antibody using techniques known in the art. Such humanized antibodies are specifically contemplated herein. In some instances it will be desired to conjugate AFAI or a portion thereof to self assembly molecules to allow for the formation of multi meric complexes having enhanced antigen-binding properties.

In an embodiment of the invention there is provided a conjugate of a polypeptide containing at least one of the three contiguous amino acid sequences and a cargo molecule or molecules. The cargo molecule may be useful for diagnosis or treatment of carcinoma. For example, it may be an enzyme or radioisotope useful in the identification and localization of cells of interest in tissue or it may be a cytotoxic agent such as a drug, further strong antigen, apoptosis inducer or radioisotope useful in reducing the viability or ability to proliferate of a carcinoma cell.

The inclusion of a reference is not an admission or suggestion that it is relevant to the patentability of anything disclosed herein.

A person understanding this invention may now conceive of alternative structures and embodiments or variations of the above all of which are intended to fall within the scope of the invention as defined in the claims that follow.

REFERENCES

1. Aina, O. H., Sroka, T. C., Chen, M. L. & Lam, K. S. (2002). Therapeutic cancer targeting peptides. *Biopolymers* 66, 184-199.
2. Hoogenboom, H. R., Henderikx, P. & de Haard, H. (1998). Creating and engineering human antibodies for immunotherapy. *Adv. Drug Deliv. Rev.* 31, 5-31.
3. Zhang, J., Spring, H. & Schwab, M. (2001). Neuroblastoma tumor cell-binding peptides identified through random peptide phage display. *Cancer Lett.* 171, 153-164.
4. Tanha, J., Dubuc, G., Hirama, T., Narang, S. A. & MacKenzie, C. R. (2002). Selection by phage display of llama conventional V(H) fragments with heavy chain antibody V(H)H properties. *J. Immunol. Methods* 263, 97-109.
5. Williams, L. E., Wu, A. M., Yazaki, P. J., Liu, A., Raubitschek, A. A., Shively, J. E. & Wong, J. Y. (2001). Numerical selection of optimal tumor imaging agents with application to engineered antibodies. *Cancer Biother. Radiopharm.* 16, 25-35.
6. Rader, C., Cheresh, D. A. & Barbas, C. F., III (1998). A phage display approach for rapid antibody humanization: designed combinatorial V gene libraries. *Proc. Natl. Acad. Sci. U.S.A* 95, 8910-8915.
7. Becerril, B., Poul, M. A. & Marks, J. D. (1999). Toward selection of internalizing antibodies from phage libraries. *Biochem. Biophys. Res. Commun.* 255, 386-393.
8. Tanha, J., Muruganandam, A. & Stanimirovic, D. (2003). Phage display technology for identifying specific antigens on brain endothelial cells. *Methods Mol. Med.* 89, 436-449.
9. Gharahdaghi, F., Weinberg, C. R., Meagher, D. A., Imai, B. S. & Mische, S. M. (1999). Mass spectrometric identification of proteins from silver-stained polyacrylamide gel: a method for the removal of silver ions to enhance sensitivity. *Electrophoresis* 20, 601-605.
10. MacKenzie R and Zhang J (2002), PCT/CA02/01829.
11. Conrath K E, Wernery U, Muyldermans S, Nguyen V K. (2003) Emergence and evolution of functional heavy-chain antibodies in Camelidae. Dev Comp Immunol. 27(2):87-103.
12. Riechmann L, Muyidermans S. (1999) Single domain antibodies: comparison of camel VH and camelised human VH domains. J Immunol Methods. 231:25-38.
13. Tanha J, Dubuc G, Hirama T, Narang S A, MacKenzie C R. (2002) Selection by phage display of llama conventional V(H) fragments with heavy chain antibody V(H)H properties. J Immunol Methods. 263:97-109.
14. Conrath K, Lauwereys M, Wyns L, Muyidermans S. (2001) Camel single-domain antibodies as modular building units in bispecific and bivalent antibody constructs. J Biol Chem. 276(10):7346-50.
15. Muyldermans S. (2001) Single domain camel antibodies: current status. J Biotechnol. 74(4):277-302.

TABLE 1

143 neoplastic lesions and 103 samples of non-neoplastic different tissue

| Categories | # | +++ | ++ | + | weak | − |
|---|---|---|---|---|---|---|
| A) LUNG NEOPLASTIC LESIONS (54 lesions) | | | | | | |
| Adenocarcinoma, nos | 22 | 8 | 11 | 3 | | |
| Undifferentiated non-small cell carcinoma | 6 | 2 | 3 | | | 1 |
| Bronchiolo-alveolar carcinoma | 7 | | 3 | 4 | | |
| Adenosquamous carcinoma | 2 | | 1 | 1 | | |
| Squamous cell carcinoma | 5 | | | | 2 | 3 |
| Undifferentiated small cell carcinoma | 3 | | | | | 3 |
| Atypical adenomatous hyperplasia | 6 | | | 1 | 3 | 2 |
| Carcinoid tumor | 3 | | | | | 3 |
| B) NON-LUNG MUCUS SECRETING TUMORS (53 tumors) | | | | | | |
| Colonic adenocarcinoma | 15 | 3 | 5 | 3 | 3 | 1 |
| Breast ductal carcinoma | 8 | | 2 | 3 | 1 | 2 |
| Pancreatic adenocarcinoma | 6 | | 2 | 1 | 2 | 1 |
| Gastric adenocarcinoma | 6 | | 1 | 2 | 1 | 2 |
| Gall bladder adenocarcinoma | 1 | | 1 | | | |
| Esophageal adenocarcinoma | 3 | | | 2 | 1 | |
| Urinary bladder adenocarcinoma | 2 | | | 1 | 1 | |

TABLE 1-continued 143 neoplastic lesions and 103 samples of non-neoplastic different tissue

| Categories | # | +++ | ++ | + | weak | − |
|---|---|---|---|---|---|---|
| Ovarian mucinous adenocarcinoma | 3 | | 1 | | | 2 |
| Trachea/adenoid cystic carcinoma | 1 | | | | | 1 |
| Urothelial carcinoma | 4 | | 1 | 1 | | 2 |
| Colonic adenoma | 4 | | 1 | 2 | | 1 |
| C) NON-LUNG AND NON-MUCINOUS TUMORS (32 tumors | | | | | | |
| Renal cell carcinoma | 4 | | 1 | | | 3 |
| Hepatocellular carcinoma | 5 | | 3 | | | 2 |
| Ovarian serous papillary carcinoma | 4 | | | | | 4 |
| Papillary thyroid carcinoma | 5 | | 1 | | | 4 |
| Salivary pleomorphic adenoma | 3 | | | | | 3 |
| Mesothelioma | 5 | | | | | 5 |
| Prostatic adenocarcinoma | 3 | | | | | 3 |
| Endometrioid carcinoma | 2 | | | | | 2 |
| Esopaheal squamous carcinoma | 1 | | | | | 1 |
| D) NORMAL LUNG TISSUE | | | | | | |
| Tissue surrounding lung carcinoma | 52 | | | | | 52 |
| Lung not harboring cancer | 4 | | | | | 4 |
| E) OTHER NORMAL TISSUES | | | | | | |
| Prostate (3), kidney (4), endometrium (2), ovary (3), thyroid (5) urinary bladder (6), esophagus (2), mesothelium (5), colonic mucosa (8), pancreas (4) gastric mucosa (5) | 47 | | | 1 a | | 46 |

Grading of the immunoreactivity:

+++: Moderate to strong immunoreactivity in more than 50% of tumor cells

++: Moderate to strong immunoreactivity in more than 10% of tumor cells

+: Moderate to strong immunoreactivity in up to 10% of tumor cells a: focal positivity in a few normal breast acini

TABLE 2

Comparison Between Non-Squamous Large Cell Lung Carcinomas And Non-Lung Carcinomas

| groups | Total | Immunoreactivity Positive | Weak or negative |
|---|---|---|---|
| Non-squamous large cell carcinomas of the lung | 35 | 34 | 1 |
| Adenocarcioma of other sites | 53 | 29 | 24 |
| (Colonic adenocarcinoma) | (15) | (11) | (4) |
| (Breast carcinoma, urothelial carcinomas and non colonic mucus-secreting adenocarcinomas)* | (38) | (18) | (20) |

*pancreas, stomach, gallbladder, ovary (non-serous), urimary bladder and esophagus The sensitivity of ES1 immunoreactivity for lung n-squamous and non-small cell carcinomas were 97% (34/35)

The specificity was 45% (24/53)

Positive predictive value: 54% (34/63)

TABLE III

Part A

```
DVQLQAGGG X1VQPGGSLRL SCAAHDPIFD KNLMGWX3RQA PGKX3X4EX5VAT ISGSGGTNYA SSVEGRFTIS RDNAKKTVYL QMNDLKPEDT AVYYCNSAFA IX6GQGTQVTV SS    SEQ ID 5
```

Part B

```
DVQLQASGGG VVQPGGSLRL SCAAHDPIFD KNLMGWGRQA PGKQREYVAT ISGSGGTNYA SSVEGRFTIS RDNAKKTVYL QMNDLKPEDT AVYYCNSAFA IWGQGTQVTV SS    SEQ. ID. 1
---S------ ---------- ---------- -----F---- ---GC-T--- ---------- ---------- ---------- ---------- ---------- -R-------- --
---D------ ---------- ---------- -----Y---- ---EQ-A--- ---------- ---------- ---------- ---------- ---------- -E-------- --
---L------ ---------- ---------- -----V---- ---DL-W--- ---------- ---------- ---------- ---------- ---------- -A-------- --
---F------ ---------- ---------- -----I---- ---LI-F--- ---------- ---------- ---------- ---------- ---------- -G-------- --
---W------ ---------- ---------- -----H---- ---RP-S--- ---------- ---------- ---------- ---------- ---------- -V-------- --
---T------ ---------- ---------- -----L---- ---KK-L--- ---------- ---------- ---------- ---------- ---------- -K-------- --
```

Part C

```
DVQLQASGGG VVQPGGSLRL SCAAHDPIFD KNLNGWGRQA PGKQREYVAT ISGSGGTNYA SSVEGRFTIS RDNAKKTVYL QMNDLKPEDT AVYYCNSAFA IWGQGTQVTV SS    SEQ. ID. 1
---D------ ---------- ---------- -----F---- ---GC-T--- ---------- ---------- ---------- ---------- ---------- -R-------- --
---L------ ---------- ---------- -----V---- ---EQ-A--- ---------- ---------- ---------- ---------- ---------- -E-------- --
---F------ ---------- ---------- -----I---- ---L-W---- ---------- ---------- ---------- ---------- ---------- -A-------- --
---W------ ---------- ---------- -----H---- ---L-F---- ---------- ---------- ---------- ---------- ---------- -G-------- --
---T------ ---------- ---------- -----L---- ---RP----- ---------- ---------- ---------- ---------- ---------- -V-------- --
---------- ---------- ---------- ---------- ---KK-L--- ---------- ---------- ---------- ---------- ---------- ---------- --
```

Part D

```
DVQLQASGGG VVQPGGSLRL SCAAHDPIFD KNLHGWGRQA PGKQREYVAT ISGSGGTNYA SSVEGRFTIS RDNAKKTVYL QMNDLKPEDT AVYYCNSAFA IWGQGTQVTV SS    SEQ. ID. 1
---------- ---------- ---------- ---------- ---GC-T--- ---------- ---------- ---------- ---------- ---------- -R-------- --
---------- ---------- ---------- ---------- ---C--T--- ---------- ---------- ---------- ---------- ---------- -R-------- --
---------- ---------- ---------- ---------- ---G--T--- ---------- ---------- ---------- ---------- ---------- -R-------- --
---------- ---------- ---------- ---------- ---GC----- ---------- ---------- ---------- ---------- ---------- -R-------- --
---------- ---------- ---------- ---------- ---GC-T--- ---------- ---------- ---------- ---------- ---------- -R-------- --
```

Part E

```
DVQLQASGGG VVQPGGSLRL SCAAHDPIFD KNLMGWGRQA PGKQREYVAT ISGSGGTNYA SSVEGRFTIS RDNAKEIVYL QMNDLKPEDT AVYYCNSAFA IWGQGTQVTV SS    SEQ. ID. 1
---D------ ---------- ---------- ---------- ---EQ-A--- ---------- ---------- ---------- ---------- ---------- -E-------- --
---D------ ---------- ---------- ---------- ---Q--A--- ---------- ---------- ---------- ---------- ---------- -E-------- --
---D------ ---------- ---------- ---------- ---E--A--- ---------- ---------- ---------- ---------- ---------- -E-------- --
---D------ ---------- ---------- ---------- ---EQ----- ---------- ---------- ---------- ---------- ---------- -E-------- --
---D------ ---------- ---------- ---------- ---EQ-A--- ---------- ---------- ---------- ---------- ---------- -E-------- --
```

Part F

```
DVQLQASGGG VVQPGGSLRL SCAAHDPIFD KNLMGWGRQA PGKQREYVAT ISGSGGTNYA SSVEGRFTIS RDHAKKTVYL QMHDLKPEDT AVYYCNSAFA IWGQGTQVTV SS    SEQ. ID. 1
---L------ ---------- ---------- -----V---- ---L-W---- ---------- ---------- ---------- ---------- ---------- -A-------- --
---L------ ---------- ---------- -----V---- ---L-W---- ---------- ---------- ---------- ---------- ---------- -A-------- --
---L------ ---------- ---------- -----V---- ---L------ ---------- ---------- ---------- ---------- ---------- -A-------- --
---L------ ---------- ---------- -----V---- ---L-W---- ---------- ---------- ---------- ---------- ---------- -A-------- --
```

TABLE III-continued

Part G

```
DVQLQASGGG VVQPGGSLRL SCAAHDPIFD ENLHGWGRQA PGKQREVAT ISGSGGTNYA SSVEGRFTIS RDNAKKTVYL QMNDLKPEDT AVYYCNSAFA IWGQGTQVTV SS    SEQ. ID. 1
---------- ---------- ---------- ---------I ---LI-F--- ---------- ---------- ---------- ---------- ---------- -G-------- --
---------- ---------F ---------- ---------I ---LI-F--- ---------- ---------- ---------- ---------- ---------- -G-------- --
---------- ---------F ---------- ---------I ----I-F--- ---------- ---------- ---------- ---------- ---------- -G-------- --
---------- ---------F ---------- ---------I ---LI----- ---------- ---------- ---------- ---------- ---------- ---------- --
---------- ---------F ---------- ---------I ---LI-F--- ---------- ---------- ---------- ---------- ---------- ---------- --
```

Part H

```
DVQLQASGGG VVQPGGSLRL SCAAHDPIFD KNLMGWGRQA PGKQREVAT ISGSGGTNYA SSVEGRFTIS RDNAKKTVYL QMNDLKPEDT AVYYCHSAFA IWGQGTQVTV SS    SEQ. ID. 1
---------- --------W- ---------- ---------H ---RP-S--- ---------- ---------- ---------- ---------- ---------- -V-------- --
---------- --------W- ---------- ---------H ----P-S--- ---------- ---------- ---------- ---------- ---------- -V-------- --
---------- --------W- ---------- ---------H ----R--S-- ---------- ---------- ---------- ---------- ---------- -V-------- --
---------- --------W- ---------- ---------H ---RP----- ---------- ---------- ---------- ---------- ---------- ---------- --
```

Part I

```
DVQLQASCGG VVQPGGSLRL SCAAHDPIFD KNLMGWGRQA PGEQREVAT ISGSGGTHYA SSVEGRFTIS RDHAKKTVYL QHNDLKPEDT AVYYCNSAFA IWGQGTQVTV SS    SEQ. ID. 1
---------- -------T-- ---------- ---------L ---KK-L--- ---------- ---------- ---------- ---------- ---------- ---------- --
---------- -------T-- ---------- ---------L ----K-L--- ---------- ---------- ---------- ---------- ---------- ---------- --
---------- -------T-- ---------- ---------L ----K-L--- ---------- ---------- ---------- ---------- ---------- ---------- --
---------- -------T-- ---------- ---------L ---KK----- ---------- ---------- ---------- ---------- ---------- ---------- --
``` wherein $X_1$ is: V, S, D, L, F, W, or T; $X_2$ is: G, F, Y, V, I, H, or L; $X_3$ is: Q, G, E, D, L, R, or K; $X_4$ is: R, C, Q, L, I, P, or K; $X_5$ is: Y, T, A, W, F, S, or L; $X_6$ is: W, R, E, A, G, V, or K.

We claim:

1. An isolated single $V_H$ domain antibody comprising complementarily determining region (CDR) 1 sequence KNLMG SEQ ID NO.4, CDR2 sequence TISGSGGTNYASSVEG SEQ ID NO.6, and CDR3 sequence AFAI SEQ ID NO.3, and wherein the isolated single domain antibody binds to non-small cell lung carcinoma.

2. A conjugate comprising the isolated single $V_H$ domain antibody of claim 1 and a cargo substance.

3. A kit comprising:
the conjugate of claim 2; and
instructions for use of the conjugate.

4. An oligomer comprising the isolated single $V_H$ domain antibody of claim 1.

5. The oligomer of claim 4 wherein subunits are linked using at least one of: a peptide linker, a self assembly molecule oligomerization domain, and chemical coupling.

6. The oligomer of claim 4 comprising at least two different subunits.

7. The oligomer of claim 4 comprising at least two identical subunits.

8. The oligomer of claim 6 wherein at least one subunit is an antibody having a different specificity than the polypeptide of SEQ ID NO:1.

9. The oligomer of claim 6 wherein at least one subunit has an enzymatic function.

10. The oligomer of claim 6 wherein at least one subunit comprises a cargo substance.

11. The isolated single $V_H$ domain antibody of claim 1, wherein the sequence comprises SEQ ID NO.1.

12. The single $V_H$ domain antibody of claim 1, wherein the CDR appear in the order listed, and wherein there is a gap of 12 to 16 amino acids between KNLMG SEQ ID NO.4 and TISGSGGTNYASSVEG SEQ ID NO.6, 30 to 34 amino acids between TISGSGGTNYASSVEG SEQ ID NO.6 and AFAI SEQ ID NO.3, and 46 to 66 amino acids between KNLMG SEQ ID NO.4 and AFAI SEQ ID NO.3.

13. The single $V_H$ domain antibody of claim 1, comprising the sequence:

DVQLQASGGGX$_1$VQPGGSLRLSCAAHDPIFDKNL MGWX$_2$RQAPGKX$_3$X$_4$EX$_5$VATISG SGGTNYASSVEGRFTISRDNAKKTVYLQMNDLKPEDTAVYY CNSAFAIX$_6$GQGTQVT VSS SEQ ID NO.5 wherein X$_1$, is: V, S, D, L, F, W, or T; X$_2$ is: G, F, Y, V, I, H, or L; X$_3$ is: Q, G, E, D, L, R, or K; X$_4$ is: R, C, Q, L, I, P, or K; X$_5$ is: Y, T, A, W, F, S, or L; X$_6$ is: W, R, E, A, G, V, or K.

14. The single $V_H$ domain antibody of claim 1, wherein the sequence comprises SEQ ID NO:2.

15. The oligomer of claim 4, wherein the isolated single $V_H$ domain antibody comprises the sequence of SEQ ID NO:1.

16. The oligomer of claim 4, wherein the isolated single $V_H$ domain antibody comprises the sequence of SEQ ID NO:2.

* * * * *